United States Patent
Zhou et al.

(10) Patent No.: US 10,354,417 B2
(45) Date of Patent: *Jul. 16, 2019

(54) MEDICAL IMAGE PROCESSING APPARATUS AND MEDICAL IMAGE DIAGNOSIS APPARATUS AND MEDICAL IMAGE PROCESSING METHOD

(71) Applicant: TOSHIBA MEDICAL SYSTEMS CORPORATION, Otawara-shi (JP)

(72) Inventors: Jian Zhou, Buffalo Grove, IL (US); Evren Asma, Buffalo Grove, IL (US); Wenli Wang, Briarcliff Manor, NY (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/858,484

(22) Filed: Dec. 29, 2017

(65) Prior Publication Data
US 2018/0144514 A1 May 24, 2018

Related U.S. Application Data

(63) Continuation-in-part of application No. 15/264,367, filed on Sep. 13, 2016, now Pat. No. 9,916,670.

(51) Int. Cl.
*G06K 9/00* (2006.01)
*G06T 11/00* (2006.01)
*G06T 7/00* (2017.01)
*A61B 6/03* (2006.01)
*A61B 6/00* (2006.01)

(52) U.S. Cl.
CPC .......... *G06T 11/005* (2013.01); *A61B 6/037* (2013.01); *A61B 6/4266* (2013.01); *G06T 7/0012* (2013.01); *G06T 11/003* (2013.01); *G06T 11/006* (2013.01); *G06T 2207/10081* (2013.01); *G06T 2207/10104* (2013.01);
(Continued)

(58) Field of Classification Search
None
See application file for complete search history.

(56) References Cited

U.S. PATENT DOCUMENTS 9,155,514 B2   10/2015   Panin et al.
9,406,154 B2    8/2016   Fu et al.
(Continued)

OTHER PUBLICATIONS

Adam S. Wang, J. Webster Stayman, and Yoshito Otake, Accelerated statistical reconstruction for C-arm cone-beam CT using Nesterov's method, Med. Phys. 42 (5), May 2015, Department of Biomedical Engineering, Johns Hopkins University, Baltimore, Maryland 21205, (revised Jan. 30, 2015; accepted for publication Feb. 8, 2015; published May 4, 2015).

(Continued)

*Primary Examiner* — Atiba O Fitzpatrick
(74) *Attorney, Agent, or Firm* — Oblon, McClelland, Maier & Neustadt, L.L.P.

(57) ABSTRACT

An embodiment provides a medical image processing apparatus that comprises circuitry. The circuitry obtains detection data representing detection events of radiation at a plurality of detector elements. The circuitry reconstructs an image by iteratively using an optimization-transfer algorithm to the detection data. The optimization-transfer algorithm uses a quadratic surrogate function that includes a curvature. The curvature is calculated using an inverse-background image.

14 Claims, 5 Drawing Sheets

(52) U.S. Cl.
CPC ............... *G06T 2207/30048* (2013.01); *G06T 2207/30096* (2013.01); *G06T 2207/30101* (2013.01)

(56) References Cited

U.S. PATENT DOCUMENTS

2014/0140599 A1   5/2014  Kim et al.
2014/0369580 A1  12/2014  Zhou et al.

OTHER PUBLICATIONS

Se Young Chun; Dewaraja, Y.K.; Fessler, J.A., "Alternating Direction Method of Multiplier for Tomography With Nonlocal Regularizers," IEEE Transactions on Medical Imaging, vol. 33, No. 10, pp. 1960-1968, Oct. 2014.

Guobao Wang; Jinyi Qi, "Edge-Preserving PET Image Reconstruction Using Trust Optimization Transfer," in Medical Imaging, IEEE Transactions on , vol. 34, No. 4, pp. 930-939, Apr. 2015.

A. R. De Pierro and M. E. B. Yamagishi, "Fast EM-like methods for maximum 'a posteriori' estimates in emission tomography," IEEE Trans. Med. Imag., vol. 20, pp. 280-288, Apr. 2001.

S. Ahn and J. Fessler, Globally convergent image reconstruction for emission tomography using relaxed ordered subsets algorithm, IEEE TMI, vol. 22, pp. 613-626, 2003.

A. R. De Pierro, "A modified expectation maximization algorithm for penalized likelihood estimation in emission tomography," IEEE Trans. Med. Imag., vol. 14, No. 1, pp. 132-137, Mar. 1995.

MEDICAL IMAGE PROCESSING APPARATUS AND MEDICAL IMAGE DIAGNOSIS APPARATUS AND MEDICAL IMAGE PROCESSING METHOD

CROSS-REFERENCE TO RELATED APPLICATIONS

This application is a Continuation-in-Part Application of U.S. patent application Ser. No. 15/264,367, filed Sep. 13, 2016, the entire contents of which are incorporated herein by reference.

FIELD

This disclosure relates to medical image processing apparatus, medical image diagnosis apparatus, and medical image processing method.

BACKGROUND

A medical image diagnosis apparatus is an imaging device such as Positron emission tomography (PET) and X-ray computed tomography imaging apparatus (X-ray CT apparatus). The medical imaging apparatus detects radiation incident to a plurality of detector elements to obtain medical data, and generates a medical image by reconstruction process using the medical data. For example, PET is an imaging device in nuclear medicine based on the use of a weak radioactively marked pharmaceutical (a tracer) in order to image certain features of a body. PET images display the spatial distribution of the radiopharmaceutical enabling a doctor or clinician to draw conclusions about metabolic activities or blood flow, for example. Therefore, PET is a functional imaging technique that has applications in oncology, cardiology, and neurology, e.g., for monitoring tumors or visualizing coronary artery disease.

In PET imaging, a tracer agent is introduced into the patient to be imaged via injection, inhalation, or ingestion. After administration, the physical and bio-molecular properties of the agent cause it to concentrate at specific locations in the patient's body. The actual spatial distribution of the agent, the intensity of the region of accumulation of the agent, and the kinetics of the process from administration to its eventual elimination are all factors that may have clinical significance.

During this process, a tracer attached to the agent will emit positrons. When an emitted positron collides with an electron, an annihilation event occurs, wherein the positron and electron are combined. Most of the time, an annihilation event produces two gamma rays (at 511 keV) traveling at substantially 180 degrees apart.

To reconstruct the spatio-temporal distribution of the tracer via tomographic reconstruction principles, each detected event is characterized for its energy (i.e., amount of light generated), its location, and its timing. By detecting the two gamma rays, and drawing a line between their locations, i.e., the line-of-response (LOR), one can determine the likely location of the original disintegration. While this process will only identify a line of possible interaction, by accumulating a large number of those lines, and through a tomographic reconstruction process, the original distribution can be estimated. The collection of a large number of events creates the necessary information for an image of a patient to be estimated through tomographic reconstruction.

Tomographic reconstruction has been widely applied to visualizing the anatomical information of patients. Tomographic reconstruction can be used in various modalities, including projection-based imaging, such as in X-ray computed tomography (CT), and emission-based imaging, such as in PET. Due to health concerns regarding exposure to radiation, doctors, scientist, and engineers in medical imaging strive to maintain radiation doses as low as reasonably possible. This effort to maintain radiation doses as low as reasonably possible motivates continued improvements in reconstructed image quality while decreasing the radiation doses and signal-to-noise ratios of the measured signals. Other constraints, in addition to concerns of dose level, motivate improvements in the computational efficiency and speed of reconstruction algorithms. For example, economic concerns and market forces motivate improvements to more efficiently employ computational resources, and desires for close to real-time feedback during surgical procedures, for example, can motivate efforts to minimize the lag time between measurements and the generation of the reconstructed image.

Statistical image reconstruction algorithms in tomography can provide improved image quality at reduced dose levels relative to more conventional reconstruction methods like filtered back-projection (FBP).

However, the statistical approach used in image reconstruction of PET imaging and X-ray CT imaging takes time due to requiring a huge amount of computational processing. To remedy the slow computationally intensive operation of standard statistical reconstruction approaches, improved methods using iterative algorithms for statistical reconstruction that converge more quickly in fewer iterations are desired.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1:
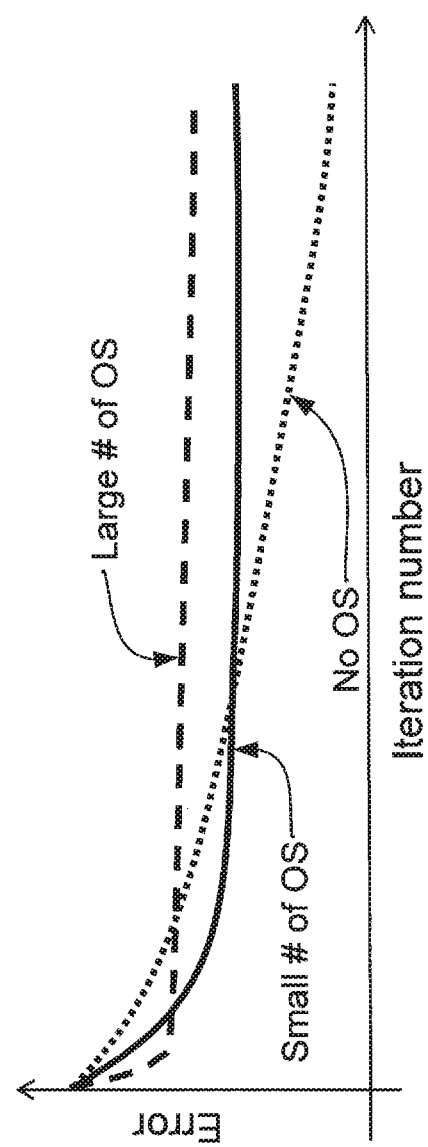
FIG. 1 shows a plot of the relative convergence rates of various expectation maximization methods, including: without ordered subset, with a small number of ordered subsets, and with a large number of ordered subsets, according to one implementation.

An embodiment provides a medical image processing apparatus that comprises circuitry. The circuitry obtains detection data representing detection events of radiation at a plurality of detector elements. The circuitry reconstructs an image by iteratively using an optimization-transfer algorithm to the detection data. The optimization-transfer algorithm uses a quadratic surrogate function that includes a curvature. The curvature is calculated using an inverse-background image.

In the following description, medical image processing apparatus, medical image diagnostic apparatus, and medical image processing method according to the embodiment will be described. Note that a case of performing reconstruction process using data detected by positron emission tomography (PET) is described as an example to exemplify description.

Not limited to this, the embodiment can be applied to a case of performing reconstruction process using data detected by X-ray CT apparatus. In addition to this, the embodiment can be applied to also a case of performing post-reconstruction by medical image processing apparatus such as medical work station using data detected by PET or X-ray CT apparatus.

Many related methods are available for statistical iterative image reconstruction for PET. Interest in iterative image reconstruction methods is partly driven by their ability to accurately model the system response and noise statistics in PET. Thus, they have been increasingly used to improve image quality. For example, the maximum likelihood (ML) method can be used to reconstruct an image from projections by maximizing the log likelihood of PET data. Related to the ML methods, penalized likelihood (PL) methods can also be used. In certain implementations, the image reconstruction problem is solved using the expectation maximization (EM) algorithm or by using an EM-like algorithm. Advantageously, the EM algorithm has a closed-form update, but the EM algorithm also suffers from slow convergence.

The above-described EM and PL methods can be used in optimization transition algorithms. Generally, optimization transition algorithms can be understood as solving the problem of finding the maximizer of an objective function:

$$\hat{x} = \underset{x}{\operatorname{argmin}} \Psi(x).$$

Using an optimization transition approach, when the objective function $\Psi(x)$ is difficult to optimize, a surrogate $\Phi(x;x^{(n)})$ is used instead, wherein, at a current iterate $x^{(n)}$, $\Phi(x;x^{(n)})$ is easier to optimize than $\Psi(x)$. Using the surrogate at a current iterate $x^{(n)}$, the surrogate can be optimized to obtain a new iterate $x^{(n+1)}$, and then the surrogate $\Phi(x;x^{(n+1)})$ can be updated for the new iterate $x^{(n+1)}$ before optimizing the surrogate $\Phi(x;x^{(n+1)})$ to obtain a newer iterate $x^{(n+2)}$, and so forth. Iteratively repeating this process, a sequence of iterates $\{x^{(n)}\}$ is generated that eventually converges to the value that optimizes the original objective function $\Psi(x)$. Mathematically, the iterative process at each step can be expressed as $$x^{(n+1)} = \underset{x}{\operatorname{argmin}} \Phi(x; x^{(n)}),$$

for $n \in \mathbb{N}$. If the surrogate $\Phi(x;x^{(n)})$ is chosen well, then the sequence $\{x^{(n)}\}$ should converge to a solution $\hat{x}$. The rate of convergence can depend on the particular surrogate chosen for the optimization transition algorithm.

Various accelerator methods can be used for tomographic image reconstruction, including ordered subsets (OS), separable quadratic surrogates (SQS), and Nesterov acceleration methods. OS methods beneficially reduce the computational cost by using only a subset of the measurement data per iteration. Additionally, separable quadratic surrogates (SQS) can be used in iterative statistical tomographic image reconstruction to more rapidly converge to an optimal solution. SQS methods can be used in an optimization transfer method together with OS methods yielding simple, efficient, and massively parallelizable methods. These combined OS and SQS methods further improve computational efficiency and performance for statistical iterative reconstruction. Further, Nesterov's acceleration method can also be used to improve computational efficiency and performance for statistical iterative reconstruction.

Although each of these improvements provides benefits, a proper choice of a quadratic surrogate in the SQS method is needed to achieve optimal results when combining the Nesterov and OS methods. When the quadratic surrogate is chosen well, the iterative reconstruction can converge more quickly than when the quadratic surrogate is chosen poorly.

Referring now to the drawings, wherein like reference numerals designate identical or corresponding parts throughout the several views, FIG. 1 shows a plot of the error of reconstructed images as a function of the iteration number for various implementations of the EM method. The dotted line labeled "No OS" refers to an implementation of the EM method without the use of ordered subsets (OS). The dashed line labeled "Large # of OS" shows the error of an implementation of the EM method using the OS technique with a large number of ordered subsets. The solid line that is labeled "Small # of OS" shows the error of an implementation of the EM method using the OS technique with a small number of ordered subsets.

The OS technique is used to accelerate the convergence rate for the EM method. As shown in FIG. 1, using the OS technique initially causes the EM method to converge more rapidly, and a larger number of ordered subsets can initially cause more rapid convergence than using a small number of ordered subsets. However, in the long run, using the OS technique can also result in slower convergence of the EM method, as shown in FIG. 1. Thus, an improvement over the OS technique by using a method that accelerates both initial convergences and long-term convergence is desirable.

Additionally, not all reconstruction methods can be used with list-mode emission data, but those that can are advantageous for PET. The methods described herein are flexible and can be used with either sinogram-based reconstruction or list-mode-based reconstruction. List-mode-based reconstruction has become increasingly popular in PET owing to the compact and natural data format. List-mode-based reconstruction is especially desirable for time-of-flight (TOF) PET imaging. However, the computational cost of list-mode-based reconstruction can depend strongly on the count level. Further, list-mode-based reconstruction can be fairly time consuming when the count level is high. Thus, iterative algorithms, such as the methods described herein, having rapid convergence to reduce the number of iterations and shorten reconstruction time, are advantageous.

The methods described herein provide list-mode-based PET reconstruction with a quadratic convergence rate. The methods described herein achieve these results by using a novel separable quadratic surrogate (SQS) function that enables precomputation of certain components. Further, the methods described herein provide low computational complexity by using only one forward-projection and one back-projection per iteration. Finally, the methods described herein can be accelerated using a combination of OS and the Nesterov accelerated gradient methods in order to achieve a quadratic convergence rate.

List-mode-based penalized likelihood reconstruction can be performed to solve the problem $$\hat{x} = \underset{x \geq 0}{\operatorname{argmin}} \Psi(x)$$

wherein $$\Psi(x) \overset{\Delta}{=} -L(x) + \beta U(x),$$

is the objective function, x is the image to be reconstructed, $L(x)$ is the Poisson likelihood function, $U(x)$ is the regularizer, and $\beta$ is a constant that weights the relative influence between the Poisson likelihood function and the regularizer. The regularizer $U(x)$ can be expressed as $$U(x) = \frac{1}{2} \sum_j v_j \sum_{l \in N_j} \omega_{lj} \rho(x_l - x_j)$$

wherein $v_j$ is a spatially variant weight that modulates the spatial noise and resolution at voxel j, $\omega_{jl}$ is the neighborhood weight for voxel j and l, and $\rho(\bullet)$ is a potential function.

The Poisson likelihood function is given by $$L(x) = -\sum_j s_j x_j + \sum_i \log([Px]_i + r_i)$$

wherein $s_j$ is the sensitivity of voxel j, P is the system matrix whose elements are denoted by $p_{ij}$ and represent the probability that the volume pixel of the reconstructed image corresponding to index j is within the line of response (LOR) associated with the $i^{th}$ detection event. Here $[\bullet]_i$ represents the $i^{th}$ element from a vector. The mean background signal is denoted by $r_i$, which includes counts due to random events and scatter events. In PET, the background signal is primarily made up of accidental coincidences (ACs), also known as randoms, and scatters.

For many annihilation events, only one photon of a pair of photons is detected because the other photons is absorbed or scattered out of plane of a PET detector ring. Further, some photon reaching the scintillating detectors of the PET detector ring are not detected due to a less than unity quantum efficiency of the detectors. Detection events in which only one of a pair of photons is detected can be referred to as "singles." If two singles from separate annihilations are detected within the coincidence timing window, then they are mistakenly registered as having arisen from the same annihilation. This is called an accidental coincidence (AC) event, also known as a random event. Stated differently, an AC event occurs when two unrelated singles are detected within a coincidence timing window.

Although most scattered photons in the body leave the detector plane undetected, some scattered photons are still detected and registered resulting in an incorrect LOR. In certain implementations, some of these scattered events resulting in incorrect LORs can be removed by energy discrimination because photons lose a fraction of their energy during the Compton interaction giving rise to the scatter event. Even so, some scattered photons (scatters) and some random coincidences (randoms) will inevitably be recorded, and, thus, the background signal r includes the randoms and the scatters.

Figure 2:
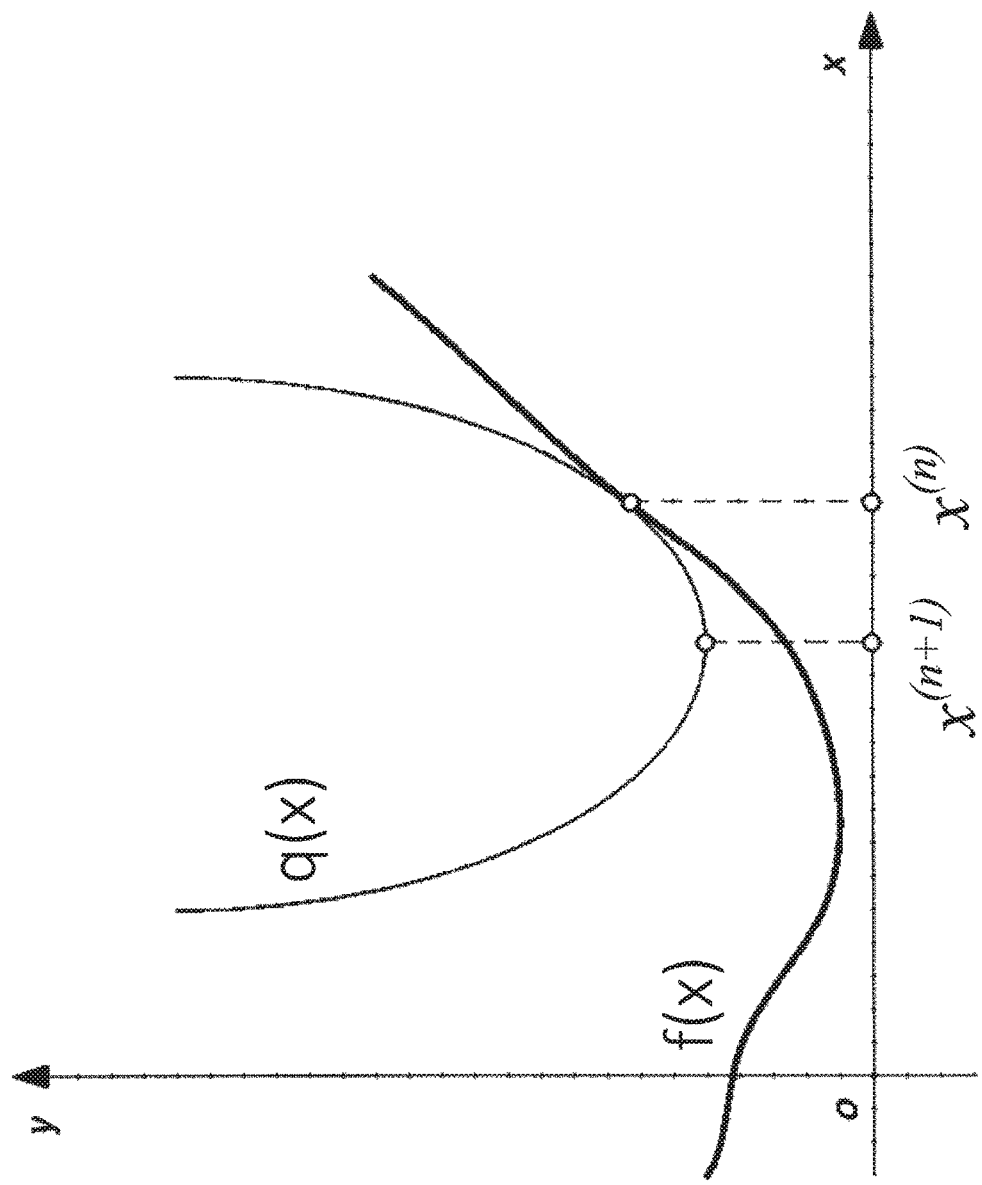
FIG. 2 shows a plot of an example of a quadratic surrogate to an objective function, according to one implementation.

Now acceleration using SQS is described with reference to the optimization transition principle described above. FIG. 2 shows a plot of an objective function $f(x)$ and a quadratic function $q(x)$ that is a surrogate to the objective function $f(x)$ at the point $x^{(n)}$. The example shown in FIG. 2 illustrates how optimization transition works to minimize an arbitrary objective function $f(x)$. During the $n^{th}$ iteration, a quadratic function $q(x)$ is constructed. The quadratic function $q(x)$ lies above the objective function $f(x)$ and has the same value and gradient as the original objective function $f(x)$ at the point $x^{(n)}$. Thus, the quadratic function $q(x)$ is defined by the constraints $$q(x) \geq f(x),$$

$$q(x^n) = f(x^n), \text{ and}$$

$$\left.\frac{dq}{dx}\right|_{x=x^{(n)}} = \left.\frac{df}{dx}\right|_{x=x^{(n)}}.$$

Then the update of the point $x^{(n+1)}$ is obtained by minimizing the quadratic function $q(x)$ at the $n^{th}$ iteration. The minimization of the quadratic function $q(x)$ can be performed rapidly due to the fact that quadratic functions such as $q(x)$ have well-known properties that allow for a closed-form solutions. At the next point $x^{(n+1)}$, another quadratic function $q(x)$ is defined according to the above constraints, and the process is repeated until the objective function $f(x)$ is optimized.

To optimize the SQS acceleration, the selection of the quadratic function $q(x)$ must strike the right balance between decreasing the total number of iterations in order to achieve convergence and keeping the per-iteration computational demands low.

For the list-mode-based PET reconstruction methods described herein, there are two separable quadratic surrogate functions $Q_L$ and $Q_U$ corresponding to the Poisson likelihood function $L(x)$ and the regularizer $U(x)$, respectively. As described for the quadratic function $q(x)$ above, the surrogate $Q_L$ is constrained to satisfy $$-L(x) \leq Q_L(x; x^{(n)}),$$

$$-L(x^{(n)}) = Q_L(x^{(n)}; x^{(n)}), \text{ and}$$

$$-\nabla_x L(x)|_{x=x^{(n)}} = \nabla_x Q_L(x; x^{(n)})|_{x=x^{(n)}},$$

wherein $x^{(n)}$ represents the image at the nth iteration. Similarly, the surrogate $Q_U$ is constrained to satisfy $$-U(x) \leq Q_U(x; x^{(n)}),$$

$$-U(x^{(n)}) = Q_U(x^{(n)}; x^{(n)}), \text{ and}$$

$$-\nabla_x U(x)|_{x=x^{(n)}} = \nabla_x Q_U(x; x^{(n)})|_{x=x^{(n)}}.$$

wherein $x^{(n)}$ represents the image at the nth iteration. The methods described herein can use any known surrogate for the regularizer $U(x)$. However, for the Poisson likelihood function $-L(x)$, a novel surrogate is proposed, which can be expressed as $$Q_L(x; x^{(n)}) =$$

$$\sum_j s_j x_j - \sum_i \log([Px]_i + r_i) - \sum_i \frac{[Px]_i - [Px^{(n)}]_i}{[Px^{(n)}]_i + r_i} + \frac{1}{2} d_j(x^{(n)})(x_j - x_j^{(n)})^2$$

wherein $d_j(x^{(n)})$ is given by $$d_j(x^{(n)}) = \frac{\gamma}{x_j^n} \sum_i \frac{p_{ij}}{r_i},$$

and γ is any positive constant satisfying the above-identified quadratic surrogate constraints (e.g., $-L(x) \leq Q_L(x;x^{(n)})$ and $-\nabla_x L(x)|_{x=x^{(n)}} = \nabla_x Q_L(x;x^{(n)})|_{x=x^{(n)}}$). The term $\Sigma_i p_{ij}/r_i$ represents a backprojection of the inverse of the mean background signal $r_i$. The same vector for the backprojection of the inverse of the mean background signal is used for all iterations for the optimization transition procedure, and does not depend on any values calculated during one of the iterations of the optimization transition procedure. Accordingly, the backprojection of the inverse of the mean background signal can be precomputed before beginning the iterative optimization transition procedure.

As discussed above, the surrogate for the Poisson likelihood term can be combined with any surrogate of the regularizer U(•). This combination of quadratic surrogates of the respective Poisson likelihood and regularizer terms forms the quadratic surrogate of the objective function for list-mode-based penalized likelihood reconstruction, which is given by $$\Phi^{SQS}(x;x^{(n)}) \triangleq Q_L(x;x^{(n)}) + \beta Q_U(x;x^{(n)}).$$

The SQS method iteratively applies the steps minimizing the quadratic surrogate for an $n^{th}$ iterate of the reconstructed image $x^{(n)}$ to generate a next iterate of the reconstructed image $x^{(n+1)}$, and then updating the quadratic surrogate using the Poisson likelihood surrogate discussed above for an $(n+1)^{th}$ iterate of the reconstructed image $x^{(n+1)}$ and so forth until convergence to the reconstructed image that minimizes the Poisson likelihood objective function $\Psi(x)$. Because the quadratic surrogate is known a priori to be quadratic, the minimization of the quadratic surrogate is simple, requiring relatively few computational resources.

In certain implementations, a Nesterov accelerated gradient implementation can be used to more rapidly converge to the reconstructed image minimizing the Poisson likelihood objective function $\Psi(x)$. In the Nesterov accelerated gradient implementation, the minimization of the quadratic surrogate can be performed according to $$x^{(n+1)} = \underset{z \geq 0}{\operatorname{argmin}} \Phi^{SQS}(z; z^{(n)}),$$

wherein the surrogate optimized to obtain the n+1$^{th}$ iterate $x^{(n+1)}$ of the reconstructed image is taken at an auxiliary image $z^{(n)}$ rather than the reconstructed image $x^{(n)}$. Further, the next quadratic surrogate is not determined using the reconstructed image $x^{(n+1)}$, but instead the quadratic surrogate is determined using an auxiliary image $z^{(n+1)}$. The auxiliary image $z^{(n+1)}$ is determined from the series of reconstructed images $\{x^n\}$ in accordance with the expression $$z^{(n+1)} = \left(1 - \frac{1}{\theta_{n+1}}\right) x^{(n+1)} + \frac{1}{\theta_{n+1}} [z^{(0)} - w]_+$$

wherein $$w = \sum_{k=0}^{n+1} \theta_k (D_k^{-1} \nabla \Phi^{SQS}(z^{(k)}; z^{(k)})),$$

n is the iteration number $$\theta_0 = 1, \text{ and } \theta_{n+1} = \frac{1 + \sqrt{1 + 4\theta_n^2}}{2},$$

and $D_k \triangleq \operatorname{diag}\{d_j(x^{(k)})\}$ is the diagonal Hessian matrix of $\Phi^{SQS}(\cdot;\cdot)$ at the $k^{th}$ iteration. In certain implementations, the auxiliary image $z^{(n)}$ can be initialized as $z^{(0)} = x^{(0)}$. The reconstructed image $x^{(0)}$ can be initialized to any image. For example, the reconstructed image $x^{(0)}$ can be initialized using an image obtained using a filtered back-projection method, or the reconstructed image $x^{(0)}$ can be initialized as an empty or uniform image. The operator $[\cdot]_+$ represents the nonnegativity constraint, which sets all negative values to zeros. Herein the constants $\theta_n$ is referred to as the Nesterov acceleration factor.

In certain implementations, an OS method can be used together with the SQS method described above and with the Nesterov acceleration described above.

Figure 3:
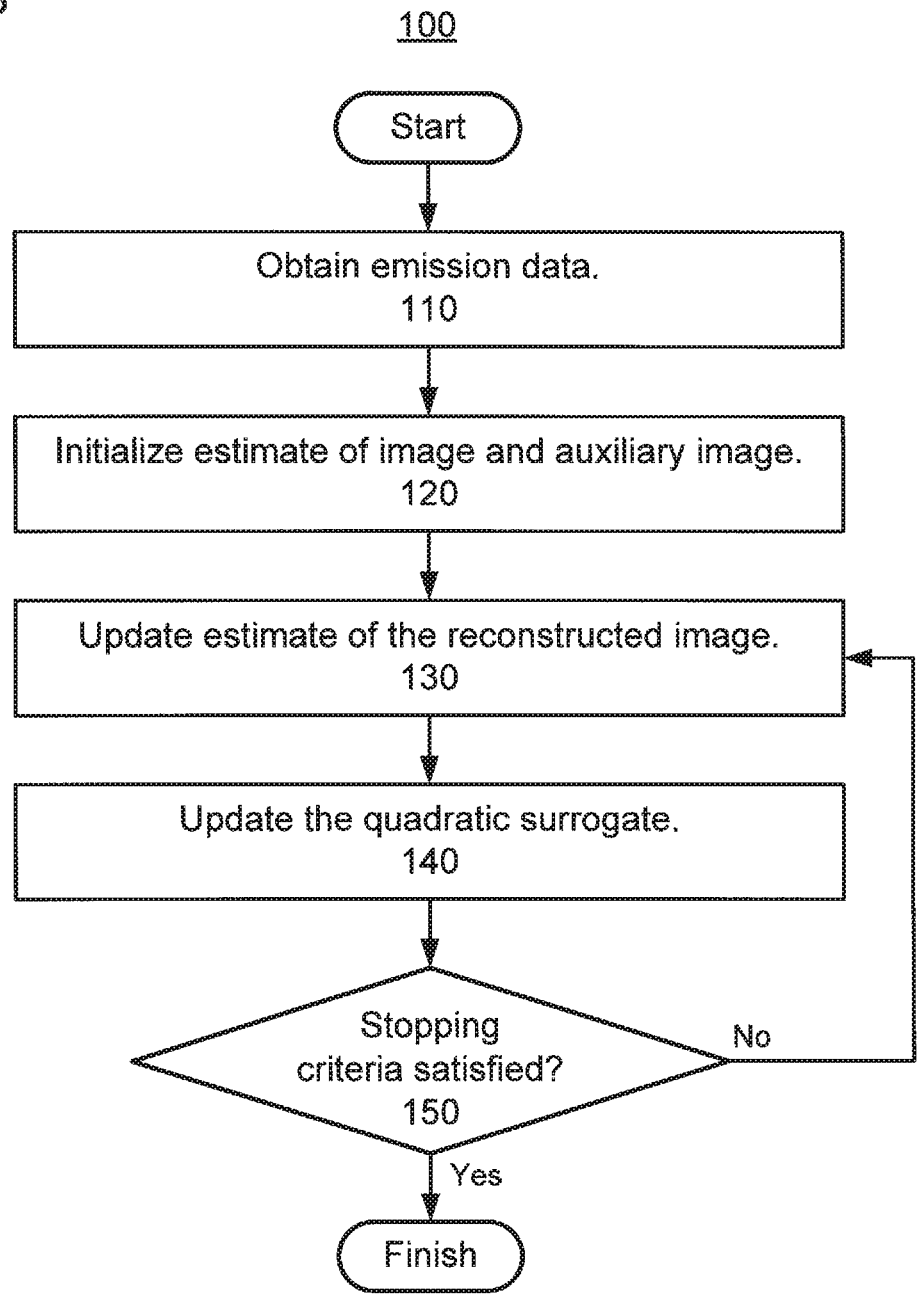
FIG. 3 shows a flow diagram of a method to iteratively reconstruct an image from emission data using quadratic surrogates.

FIG. 3 shows a flow chart of a method 100 for iteratively reconstructing an image using a quadratic surrogate that includes a background-based curvature term $d_j(x^{(n)})$. The curvature is calculated by using an inverse background-based image. The inverse background image is generated based on the background-based signal.

In step 110 of method 100, the emission data is obtained. For example, the data can be obtained using a PET apparatus, or by recalling from memory emission data that has been previously obtained. The emission data can be either sinogram data or list-mode data.

In step 120 of method 100, the starting reconstructed image $x^0$ and auxiliary image $z^0$ are initialized. Additionally, other factors such as the loop variable n and the constant ) are initialized and selected, and the back-projection of the inverse of the mean background $\frac{1}{r_i}$ can be precomputed. Additionally, the quadratic surrogate of the objective function can be determined at the initial reconstructed image $x^0$.

In step 130 of method 100, the quadratic surrogate of the objective function is minimized in order to update the reconstructed image for the current iteration indicated by the loop variable n.

In step 140 of method 100, the quadratic surrogate is updated according to the updated reconstructed image for the current iteration. Without Nesterov acceleration, the updated quadratic surrogate is determined using the updated reconstructed image $x^{n+1}$. With Nesterov acceleration, the updated quadratic surrogate is determined using the updated auxiliary image $z^{n+1}$.

In step 150 of method 100, stopping criteria is evaluated. For example, the stopping criteria can include a convergence criterion and/or a maximum number of iterations criterion. If the stopping criteria are satisfied, then method 100 is complete. Otherwise, method 100 returns from step 150 to step 130 to repeat the updating steps 130 and 140.

Figure 4:
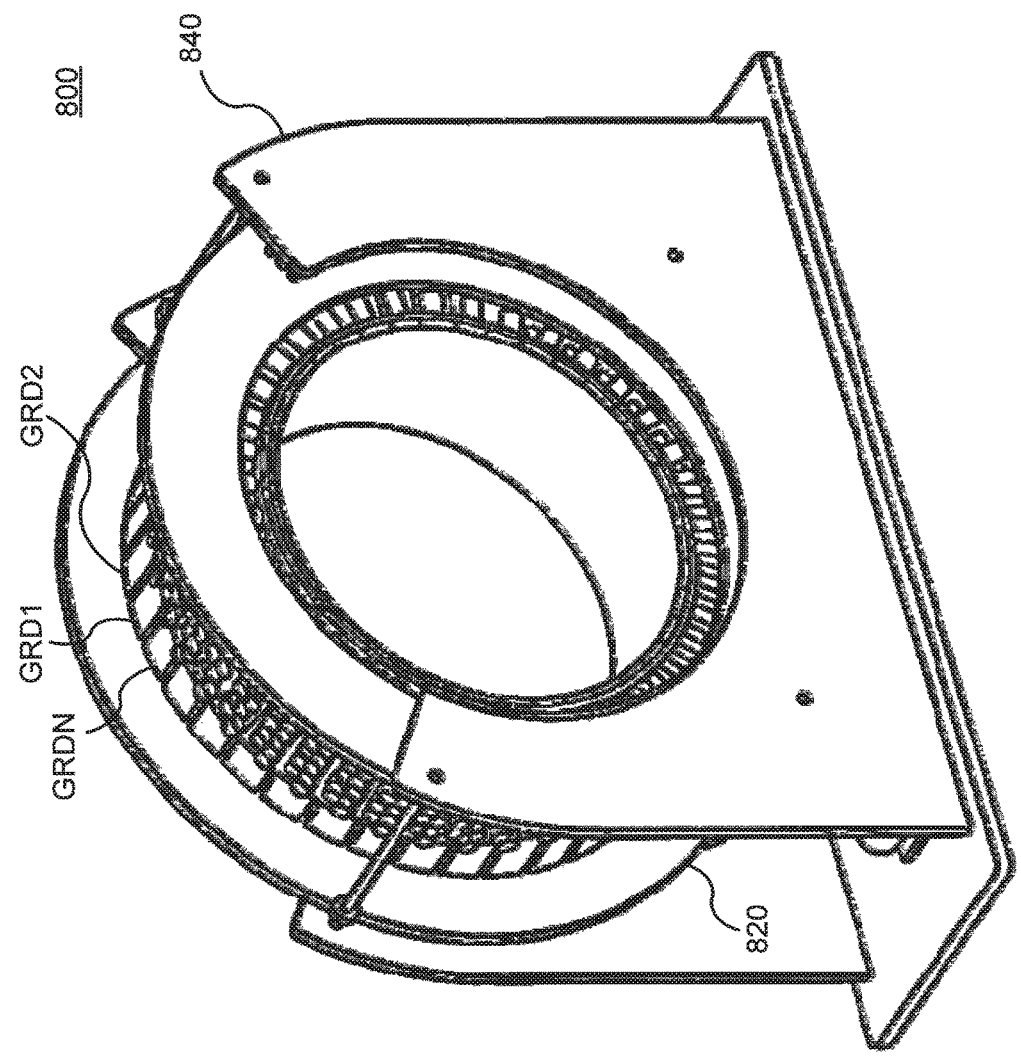
FIG. 4 shows a perspective view of a positron-emission tomography (PET) scanner, according to one implementation.
Figure 5:
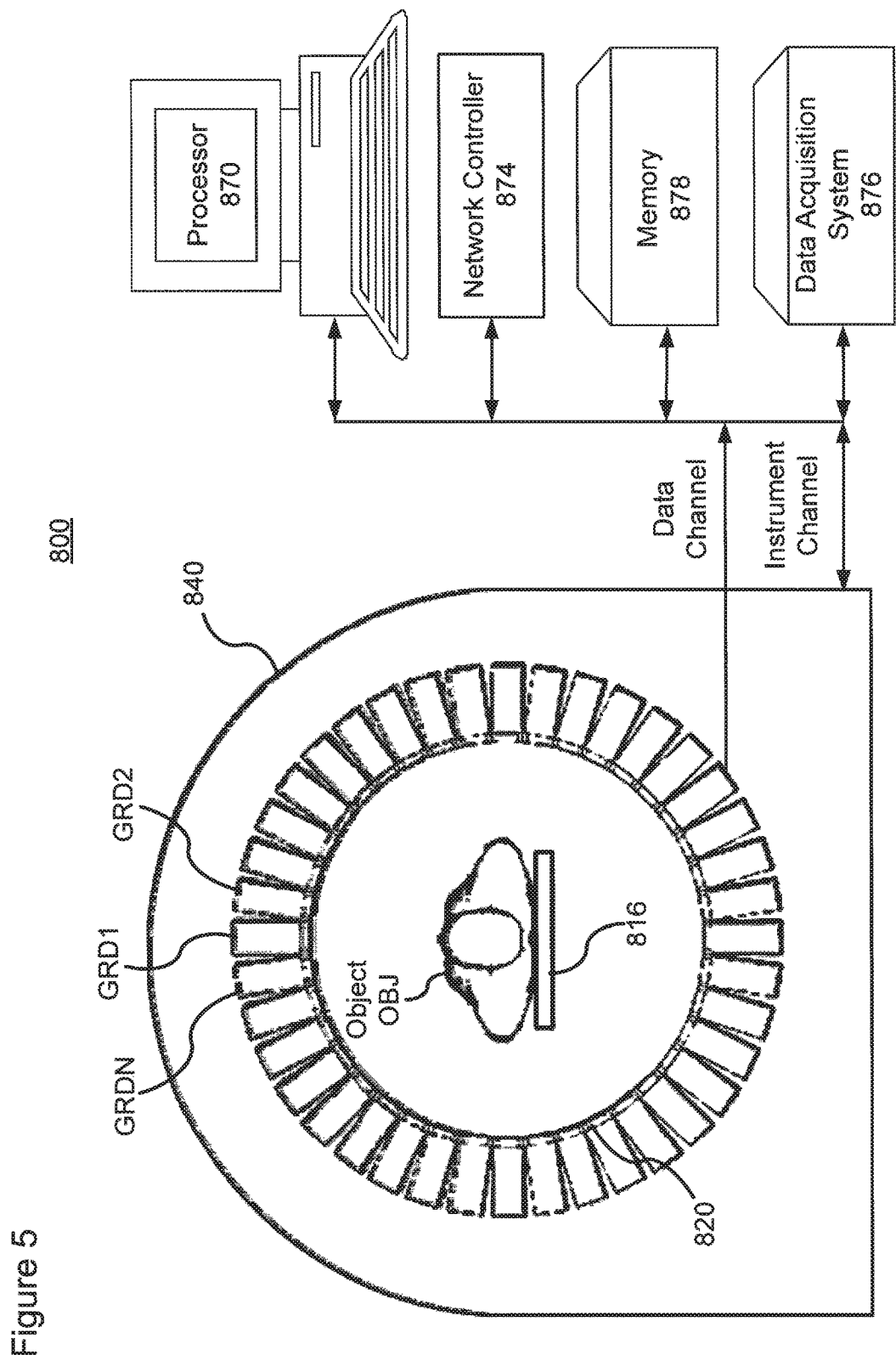
FIG. 5 shows a schematic view of the PET scanner, according to one implementation.

FIGS. 4 and 5 show a PET scanner 800 including a number of GRDs (e.g., GRD1, GRD2, through GRDN) that are each configured as rectangular detector modules. According to one implementation, the detector ring includes 40 GRDs. In another implementation, there are 48 GRDs, and the higher number of GRDs is used to create a larger bore size for the PET scanner 800.

Each GRD can include a two-dimensional array of individual detector crystals, which absorb gamma radiation and emit scintillation photons. The scintillation photons can be detected by a two-dimensional array of photomultiplier tubes (PMTS) that are also arranged in the GRD. A light guide can be disposed between the array of detector crystals and the PMTs. Further, each GRD can include a number of PMTs of various sizes, each of which is arranged to receive scintillation photons from a plurality of detector crystals. Each PMT can produce an analog signal that indicates when scintillation events occur, and an energy of the gamma ray producing the detection event. Moreover, the photons emitted from one detector crystal can be detected by more than one PMT, and, based on the analog signal produced at each PMT, the detector crystal corresponding to the detection event can be determined using Anger logic and crystal decoding, for example.

FIG. 5 shows a schematic view of a PET scanner system having gamma-ray (gamma-ray) photon counting detectors (GRDs) arranged to detect gamma-rays emitted from an object OBJ. The GRDs can measure the timing, position, and energy corresponding to each gamma-ray detection. In one implementation, the gamma-ray detectors are arranged in a ring, as shown in FIGS. 4 and 5. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 5 shows an example of the arrangement of the PET scanner 800, in which the object OBJ to be imaged rests on a table 816 and the GRD modules GRD1 through GRDN are arranged circumferentially around the object OBJ and the table 816. The GRDs can be fixedly connected to a circular component 820 that is fixedly connected to the gantry 840. The gantry 840 houses many parts of the PET imager. The gantry 840 of the PET imager also includes an open aperture through which the object OBJ and the table 816 can pass, and gamma-rays emitted in opposite directions from the object OBJ due to an annihilation event can be detected by the GRDs and timing and energy information can be used to determine coincidences for gamma-ray pairs.

In FIG. 5, circuitry and hardware is also shown for acquiring, storing, processing, and distributing gamma-ray detection data. The circuitry and hardware include: a processor 870, a network controller 874, a memory 878, and a data acquisition system (DAS) 876. The PET imager also includes a data channel that routes detection measurement results from the GRDs to the DAS 876, a processor 870, a memory 878, and a network controller 874. The data acquisition system 876 can control the acquisition, digitization, and routing of the detection data from the detectors. In one implementation, the DAS 876 controls the movement of the table 816. The processor 870 performs functions including reconstructing images from the detection data in accordance with method 100, pre-reconstruction processing of the detection data, and post-reconstruction processing of the image data, as discussed herein.

The processor 870 can be configured to perform method 100 described herein. The processor 870 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 870 can execute a computer program including a set of computer-readable instructions that perform method 100 described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, and other predetermined operating systems known to those skilled in the art. Further, CPU can be implemented as multiple processors cooperatively working in parallel to perform the instructions.

In one implementation, the reconstructed image can be displayed on a display. The display can be an LCD display, CRT display, plasma display, OLED, LED or any other display known in the art.

The memory 878 can be a hard disk drive, CD-ROM drive, DVD drive, FLASH drive, RAM, ROM or any other electronic storage known in the art.

The network controller 874 can interface between the various parts of the PET imager. Additionally, the network controller 874 can also interface with an external network. As can be appreciated, the external network can be a public network, such as the Internet, or a private network such as an LAN or WAN network, or any combination thereof and can also include PSTN or ISDN sub-networks. The external network can also be wired, or can be wireless such as a cellular network including EDGE, 3G and 4G wireless cellular systems. The wireless network can also be any other wireless form of communication.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. A positron emission tomography (PET) processing apparatus, comprising:
    circuitry configured to
        obtain detection data representing detection events of radiation at a plurality of detector elements, and
        reconstruct an image by iteratively using an optimization-transfer algorithm to the detection data, the optimization-transfer algorithm using a quadratic surrogate function that includes a curvature, the curvature being calculated using an inverse-background image.

2. The PET processing apparatus according to claim 1, wherein the circuitry is further configured to obtain the inverse-background image by calculating a back-projection of an inverse of background detection data representing random detection events and scatter detection events.

3. The PET processing apparatus according to claim 2, wherein the circuitry is further configured to obtain the inverse-background image by replacing values of the background detection data less than a predefined threshold by a predefined positive value.

4. The PET processing apparatus according to claim 1, wherein the circuitry is further configured to reconstruct the image using a Nesterov acceleration factor that is updated for each iteration of the optimization-transfer algorithm.

5. The PET processing apparatus according to claim 2, wherein the circuitry is further configured to iteratively perform the optimization-transfer algorithm using pre-calculated the inverse background image.

6. The PET processing apparatus according to claim 2, wherein the circuitry is further configured to reconstruct the image using the quadratic surrogate function.

7. The PET processing apparatus according to claim 1, wherein the circuitry is further configured to iteratively use the optimization-transition algorithm, for each iteration, using the quadratic surrogate function that includes the curvature that is calculated based on a pixel of the reconstructed image, a pixel of the inverse background image, and predetermined constant factor.

8. The PET processing apparatus according to claim 7, wherein the predetermined constant factor is in a range to ensure the quadratic surrogate function satisfies quadratic surrogate constraints.

9. The PET processing apparatus according to claim 1, wherein the circuitry further configured to update the reconstructed image by optimizing an objective function obtained using the quadratic surrogate function and an auxiliary image from a previous iteration.

10. The PET processing apparatus according to claim 1, wherein the circuitry is further configured to, by using the quadratic surrogate function,
calculate a first intermediate value of the current iteration based on a difference between a first intermediate value of the previous iteration and a second intermediate value, and
calculate the second intermediate value based on a Nesterov acceleration factor and a vector product, the vector product being between an inverse of a diagonal Hessian matrix of the reconstructed image of the current iteration and a gradient of the reconstructed image of the current iteration.

11. The PET processing apparatus according to claim 10, wherein the circuitry is further configured to
calculate, during the current iteration, the Nesterov acceleration factor as one-half of a first intermediate value, and
calculate, during the current iteration, the first intermediate value as one plus a square root of one plus four times a square of the Nesterov acceleration factor of the previous iteration.

12. The PET processing apparatus according to claim 10, wherein the circuitry is further configured to update an auxiliary image by, for the current iteration,
calculating the first vector as a product between an updated reconstructed image and a difference between one and an inverse of the Nesterov acceleration factor for the current iteration,
calculating the second vector as a product between the first intermediate value and an inverse of the Nesterov acceleration factor for the current iteration, and calculating, a sum between the first vector and the second vector.

13. A positron emission tomography (PET) diagnosis apparatus, comprising:
a detector configured to detect detection events using a plurality of detector elements; and
circuitry configured to
obtain detection data representing detection events of radiation at a plurality of detector elements, and
reconstruct an image by iteratively using an optimization-transfer algorithm to the detection data, the optimization-transfer algorithm using a quadratic surrogate function that includes a curvature, the curvature being calculated using an inverse-background image.

14. An method, comprising:
obtaining detection data representing detection events of radiation at a plurality of detector elements, and
reconstructing an image by iteratively using an optimization-transfer algorithm to the detection data, the optimization-transfer algorithm using a quadratic surrogate function that includes a curvature, the curvature being calculated using an inverse-background image.

* * * * *